United States Patent [19]

Snipes et al.

[11] Patent Number: 4,696,817

[45] Date of Patent: Sep. 29, 1987

[54] EXTRACTION OF TEICHOMYCIN $A_2$ FROM WHOLE CULTURE FERMENTATION BROTH

[75] Inventors: Carl E. Snipes; John S. Coleman, both of Midland, Mich.

[73] Assignee: The Dow Chemical Company, Midland, Mich.

[21] Appl. No.: 540,266

[22] Filed: Oct. 11, 1983

[51] Int. Cl.$^4$ ............................................. A61K 35/74
[52] U.S. Cl. ...................................................... 424/123
[58] Field of Search ......................... 424/118, 123, 124

[56] References Cited

U.S. PATENT DOCUMENTS 4,239,751 12/1980 Coronelli et al. .................... 424/118

OTHER PUBLICATIONS

Bardone et al, J. of Antibiotics, vol. XXXI, No. 3, Mar. 1978, pp. 170–177.

Primary Examiner—Jerome D. Goldberg
Attorney, Agent, or Firm—Joseph T. Majka; Ronald G. Brookens

[57] ABSTRACT

Teichomycin $A_2$ is recovered from whole culture fermentation broth of *Actinoplanes teichomyceticus sp.* or any similar microorganism producing Teichomycin $A_2$ by extracting the broth with a water miscible solvent, such as acetone, acetonitrile, dimethylsulfoxide, n-propanol, methyl ethyl ketone or mixtures thereof.

19 Claims, No Drawings

4,696,817

EXTRACTION OF TEICHOMYCIN A₂ FROM WHOLE CULTURE FERMENTATION BROTH

BACKGROUND OF THE INVENTION

The present invention relates to a method of extracting Teichomycin $A_2$ from a whole culture fermentation broth with a suitable water miscible solvent.

U.S. Pat. No. 4,239,751 discloses the antibiotic Teichomycin $A_2$ which is obtained by cultivation of strain *Actinoplanes teichomyceticus* nov. sp. ATTC 31121. Under the nomenclature established in the World Health Organization Handbook for International Non-Proprietary Names (INN), the name "Teichomycin $A_2$" has been changed to "Teicoplanin" as the most recent name for this antibiotic factor. Teichomycin $A_2$ is one of a mixture of antibiotic factors Teichomycin $A_1$, and Antibiotic 8327 Factor C produced by this strain. U.S. Pat. No. 4,239,751 teaches a method of isolating the antibiotic factors. In the method described in U.S. Pat. No. 4,239,751, the fermentation broth is filtered in order to remove the mycelial cell mass, leaving a mycelial cake. The filtered fermentation broth is then mixed with a water immiscible organic solvent, such as, halogenated $C_1$–$C_4$ hydrocarbons or $C_4$–$C_6$ alkanols, in which the antibiotic mixture is soluble. The water immiscible organic solvent is then separated from the filtered fermentation broth by high-speed centrifugation, concentrated to about 1/10 to 1/20 of its original volume, cooled and allowed to stand until a precipitate (the antibiotic) forms which is recovered by filtration. Additional product may be recovered by extracting the mycelial cake with aqueous acetone. After distillation of the acetone, the aqueous phase is submitted to the same treatment described above for the filtered fermentation broth.

SUMMARY OF THE INVENTION

Briefly, in accordance with the present invention, Teichomycin $A_2$ is extracted from whole culture fermentation broth of *Actinoplanes teichomyceticus* or any similar microorganism producing Teichomycin $A_2$ containing a mycelial mass, by a process comprising mixing the broth containing the mycelial mass with an effective amount of a water miscible solvent to accumulate Teichomycin $A_2$ in the broth/solvent liquid; separating the broth/solvent liquid containing accumulated Teichomycin $A_2$ from the mycelial mass; and precipitating and separating Teichomycin $A_2$ from the broth/solvent liquid. The useful water miscible solvents include acetone, acetonitrile, dimethylsulfoxide, n-propanol, methyl ethyl ketone or mixtures of these solvents.

The present extraction process is carried out by mixing an effective amount of a solvent, described above, with whole culture fermentation broth of *Actinoplanes teichomyceticus* which contains Teichomycin $A_2$. The solvent and broth are thoroughly contacted for an effective time period whereby the Teichomycin $A_2$ is accumulated in the liquid solvent/broth mixture. The Teichomycin $A_2$ is then recovered from this liquid employing standard separatory and purification techniques.

DETAILED DESCRIPTION OF THE INVENTION

The present invention employs a whole culture fermentation broth of *Actinoplanes teichomyceticus* containing Teichomycin $A_2$. Water miscible solvent used to accumulate Teichomycin $A_2$ in the broth/solvent liquid include acetone, acetonitrile, dimethylsulfoxide (DMSO), n-propanol, methyl ethyl ketone (MEK) and mixtures of these solvents.

The preparation of Teichomycin $A_2$ by the fermentation of *Actinoplanes teichomyceticus* is described in U.S. Pat. No. 4,239,751 which is incorporated herein by reference. The whole culture fermentation broth containing the cell mass, aqueous nutrient medium and the Teichomycin $A_2$, is treated according to the present invention after the fermentation is complete.

The solvents employed in the practice of the present invention include: acetone, acetonitrile, DMSO, n-propanol or MEK. Mixtures of these solvents can also be used. The solvents are employed in amounts between about 5 to about 80 percent by volume based on the total volume of solvent and broth, i.e., solvent/broth ratio of from about 1/19 to about 4/1. Preferably, from about 10 to about 60 percent by volume of solvent is employed. Preferred solvents are acetone and n-propanol.

The present invention is advantageously conducted at ambient temperatures and ambient pressures. The mixing is typically conducted with mild agitation sufficient to maintain a thorough contacting of fermentation broth and solvent. The pH of the fermentation broth is not critical to the present process. An acidic pH is preferred and it is especially preferred that the pH of the fermentation broth be in the range of from about 3 to about 4. The pH of the fermentation broth can be adjusted by the addition of an acid or base. Suitable acids include $H_2SO_4$, HCl, acetic acid and formic acid. Suitable bases include alkali metal bases, such as, NaOH or KOH.

In conducting the extraction process, an effective amount of the herein described solvents is mixed with whole culture fermentation broth of *Actinoplanes teichomyceticus*, which contains Teichomycin $A_2$, for an effective time period to accumulate the Teichomycin $A_2$ in the mixed fermentation broth/solvent liquid. The rate of mixing the solvent and the fermentation broth is not critical. Preferably the solvent is added to the fermentation broth. An effective mixing time period is usually achieved in from about 2 to about 60 minutes.

After completion of the mixing period, the fermentation broth/solvent liquid is separated from the mycelial mass by centrifugation or filtration. The fermentation broth/solvent liquid separated from the mycelial cake, hereinafter referred to as "supernatant", is then concentrated, for example, to about ½ to 1/10 of its original volume, cooled and allowed to stand until a precipitate forms. The precipitate, containing Teichomycin $A_2$, is then recovered from the supernatant by filtration. Alternatively, Teichomycin $A_2$ can be recovered from the supernatant concentrated as described hereinabove, followed by acid precipitation.

In a preferred embodiment of the present invention, acetone or n-propanol is added to whole culture fermentation broth of *Actinoplanes teichomyceticus* which contains Teichomycin $A_2$ whereby the acetone or n-propanol represents from about 20 to about 50% by volume of the mixture. The mixture is agitated, from about 2 to about 60 minutes, such as by stirring or shaking to cause a thorough mixing of the acetone or n-propanol with the fermentation broth. The fermentation broth/solvent liquid is separated from the mycelial mass by centrifuging or filtering. Teichomycin $A_2$ is isolated from the supernatant by concentrating the supernatant to ½-1/10 its original volume, cooling the concentrate and allowing it to stand until a precipitate forms. The precipitate is Teichomycin $A_2$ which is collected by standard separation techniques such as filtration.

The following examples illustrate the practice of the present invention but should not be construed as limiting its scope.

EXAMPLE 1

Samples (3 ml each) from whole culture fermentation broth (pH=6.8–7) of *Actinoplanes teichomyceticus* were mixed with volumes of acetonitrile to give from 20 to 60 percent by total volume mixtures of the acetonitrile in fermentation broth. After a 5 minute mixing period with continuous agitation, the samples were centrifuged and the supernatant was assayed for Teichomycin $A_2$ employing standard high pressure liquid chromatography (HPLC) methods employing:
Column: DuPont ZORBAX ® 4.6 mm×25 cm ODS
Flow: 1.8 ml/min.
Solvent: 24.5/75.5 acetonitrile/0.03 $\overline{M}$ ammonium formate at pH 6.0
Absorbance: 254 mm
The results are listed below:

| % Acetonitrile (by volume) | Teichomycin $A_2$ (μg/ml) |
|---|---|
| 50 | 235 |
| 40 | 263 |
| 30 | 269 |
| 20 | 254 |
| Control (no solvent) | 98 |

EXAMPLE 2

Employing substantially the same procedures of Example 1, various water miscible solvents contemplated by the present invention were used to extract Teichomycin $A_2$ from samples of whole culture fermentation broth of *Actinoplanes teichomyceticus*. The fermentation broth had a pH of 6.0. The results are listed below:

| Solvent (Percent by volume) | Teichomycin $A_2$ (μg/ml) |
|---|---|
| Control (no solvent) | 124 |
| 20% acetonitrile | 383 |
| 20% acetone | 317 |
| 30% acetone | 366 |
| 40% acetone | 392 |
| 50% acetone | 303 |
| 20% n-propanol | 328 |
| 30% n-propanol | 445 |
| 40% n-propanol | 487 |
| 50% n-propanol | 318 |
| 10% MEK* | 215 |
| 15% MEK* | 256 |
| 20% MEK* | 325 |
| 25% MEK* | 379 |

*MEK represents methyl ethyl ketone

The supernatant fluids containing high levels of Teichomycin $A_2$ from Examples 1 and 2 above are then treated to isolate the Teichomycin $A_2$. The supernatant fluids are concentrated to from about ½ to about 1/10 their original volume, cooled and allowed to stand until a precipitate forms. The precipitate, containing Teichomycin $A_2$, is recovered by filtration from the supernatant.

The Teichomycin $A_2$ recovered employing the procedures of the present invention is then used for known uses, such as, an antibiotic.

We claim:
1. A method of extracting Teichomycin $A_2$ from a whole culture fermentation broth containing a mycelial mass comprising
    (a) mixing the broth containing the mycelial mass with an effective amount of a water miscible solvent,
    (b) agitating the mixture for a time sufficient to accumulate the Teichomycin $A_2$ in the broth/solvent liquid,
    (c) separating the broth/solvent liquid containing the accumulated Teichomycin $A_2$ from the mycelial mass,
    (d) reducing the volume of the broth/solvent liquid to concentrate the Teichomycin $A_2$,
    (e) precipitating the Teichomycin $A_2$ in the reduced volume of broth/solvent liquid, and
    (f) separating the precipitated Teichomycin $A_2$ from the broth/solvent liquid.
2. The method of claim 1 wherein the water miscible solvent is acetone, n-propanol, acetonitrile, methyl ethyl ketone, dimethylsulfoxide, or mixtures thereof.
3. The method of claim 2 wherein the water miscible solvent is acetone.
4. The method of claim 2 wherein the water miscible solvent is n-propanol.
5. The method of claim 1 wherein the solvent is between about 5 to about 80 percent of the volume of the broth/solvent liquid.
6. The method of claim 5 wherein the solvent is between about 10 to about 60 percent of the volume of the broth/solvent liquid.
7. The method of claim 1 wherein the water miscible solvent is mixed with an acidic fermentation broth.
8. The method of claim 7 wherein the acidity of the fermentation broth is set to a pH of about 3 to about 4.
9. The method of claim 7 wherein the acidity of the fermentation broth is adjusted to a desired pH using an acid selected from the group consisting of sulfuric acid, hydrochloric acid, acetic acid, and formic acid.
10. The method of claim 1 wherein the water miscible solvent is mixed with an alkaline fermentation broth.
11. The method of claim 10 wherein the alkalinity of the fermentation broth is adjusted by an alkali metal base.
12. The method of claim 11 wherein the alkali metal base is sodium hydroxide or potassium hydroxide.
13. The method of claim 1 wherein the agitating of the fermentation broth and the water miscible solvent is carried out for a time of at least 2 minutes.
14. The method of claim 13 wherein the agitating is carried out from about 2 minutes to about 60 minutes.
15. The method of claim 1 wherein the broth/solvent liquid containing the accumulated Teichomycin $A_2$ is separated from the mycelial mass by centrifugation.
16. The method of claim 1 wherein the broth/solvent liquid containing the accumulated Teichomycin $A_2$ is separated from the mycelial mass by filtration.
17. The method of claim 1 wherein the Teichomycin $A_2$ is precipitated by reducing the volume of the broth/solvent liquid after its separation from the mycelial mass to about ½ to about 1/10th of its original volume, cooling the concentrated liquid and allowing the concentrated liquid to stand until a precipitate forms.
18. The method of claim 1 wherein the Teichomycin $A_2$ is precipitated by acidifying the broth/solvent liquid after reducing the volume of the broth/solvent liquid.
19. The method of claim 1 wherein the precipitated Teichomycin $A_2$ is separated from the broth/solvent liquid by filtration.

* * * * *